| United States Patent [19] | [11] Patent Number: 4,769,329 |
|---|---|
| Cooper et al. | [45] Date of Patent: Sep. 6, 1988 |

[54] PREPARATION OF OPTICALLY PURE D- AND L- LACTIC ACID

[75] Inventors: Bryan Cooper; Werner Kuesters, both of Ludwigshafen; Christoph Martin, Mannheim; Hardo Siegel, Speyer, all of Fed. Rep. of Germany

[73] Assignee: BASF Aktiengesellschaft, Ludwigshafen, Fed. Rep. of Germany

[21] Appl. No.: 393,630

[22] Filed: Jun. 30, 1982

[30] Foreign Application Priority Data

Jul. 2, 1981 [DE] Fed. Rep. of Germany ....... 3126021

[51] Int. Cl.⁴ .......................... C12P 29/00; C12P 7/56; C12R 1/85; C12R 1/09
[52] U.S. Cl. ...................................... 435/139; 435/42; 435/253; 435/256; 435/835; 435/940
[58] Field of Search ................ 435/42, 139, 253, 256, 435/853, 940

[56] References Cited

U.S. PATENT DOCUMENTS

| 1,980,083 | 11/1934 | Owen | 435/885 |
|---|---|---|---|
| 2,132,712 | 10/1938 | Ward et al. | 435/139 |
| 3,262,862 | 7/1966 | Kitahara | 435/139 |
| 3,494,832 | 2/1970 | Florent et al. | |
| 3,983,008 | 9/1976 | Shinozaki et al. | 435/287 |
| 4,018,650 | 4/1977 | Busta et al. | 435/832 |
| 4,305,963 | 12/1981 | Nakagawa | 426/64 |

FOREIGN PATENT DOCUMENTS 1642738 5/1966 Fed. Rep. of Germany .
2273064 12/1975 France .
1030740 5/1966 United Kingdom .

OTHER PUBLICATIONS

J. Appl. Bacteriol. 23 (1960), pp. 130–135.
De Man, J. C. et al., *Jour. Appl. Bact.,* vol. 23, (1), pp. 130–135 (1960), "A Medium for the Cultivation of Lactobacilli".
*Chemical Abstracts,* vol. 23, Abstract No. 3948-5, Neill, J. M. et al., "The Use of Culture Media Made from Commercial Dried Yeast as a Routine Substitute for Meat Infusion Peptone Media".
*Chemical Abstracts,* vol. 65, No. 3, 1966, Abstract No. 4616c, Krumphanzl, V. et al., "Lactic Acid".
*Chemical Abstracts,* vol. 82, 1975, p. 445, Abstract No. 56031w, Fujino, S. et al., "Preparation of Yeast Extract by Cell Wall Lytic Enzymes".
*The Yeasts,* vol. 3, Rose, A. H. et al., editors, "Mixed Culture of Saké Yeast and Saké Lactic Acid Bacteria", Chapter 5, pp. 235–237, Academic Press, New York (1970).
Chemical Abstracts 29, 1128-5 (1935).

*Primary Examiner*—Thomas G. Wiseman
*Assistant Examiner*—Robin Lyn Teskin
*Attorney, Agent, or Firm*—Keil & Weinkauf

[57] ABSTRACT

A process for the preparation of optically pure D- or L-lactic acid by fermentation of an aqueous nutrient medium, which contains nitrogen, vitamins, aminoacids, sugars and trace elements, by means of a microorganism, at pH 4–6, wherein the nutrient medium contains brewers' yeast as the source of nitrogen, vitamins, aminoacids and trace elements.

3 Claims, No Drawings

PREPARATION OF OPTICALLY PURE D- AND L-LACTIC ACID

The present invention relates to a novel process for the preparation of optically pure D- and L-lactic acid by fermentation.

The preparation of Lactic acid by fermentation of sugars with bacteria of the genus Lactobacillus has been known for a long time. These industrial fermentation processes do not produce optically pure lactic acid but racemic mixtures which are employed in substantial amounts in the foodstuff industry.

However, racemic Lactic acid is unsuitable as a starting material for the preparation of optically pure active ingredients for the pharmaceutical and crop protection sectors, optically pure D- or L-lactic acid being required in these cases.

Attempts have been made to prepare optically pure lactic acid using *Lactobacillus* species. These require for their growth a number of substances which they cannot produce themselves, for example biotin, thiamine, nicotinic acid, pyridoxamine, p-aminobenzoic acid, pantothenic acid and cyanocobalamin, and these compounds are added in the form of complex substrates to the nutrient medium. For example, Lactobacilli are grown on a laboratory scale using the complex medium (MRS medium) developed by de Man, Rogosa and Sharpe (J. Appl. Bacteriol. 23 (1960), 130) and containing the following constituents: peptone, meat extract, yeast extract, Tween 80 $^R$, sodium acetate, triammonium citrate, $MgSO_4$, $MnSO_4$ and and $K_2HPO_4$.

However, this medium is unsuitable for the industrial production of lactic acid, since the complex substrates used are excessively expensive and materials of constant quality are not available in the required amounts. Complex substrates, such as sugar-beet molasses or corn steep liquor, are therefore added to the industrial nutrient solutions (German Laid-Open Application DOS No. 1,642,738). Although these substrates stimulate the growth of the bacteria, they cannot be used for the preparation of optically pure lactic acid because they themselves contain a substantial amount of racemic lactic acid. Optically pure Lactic acid can be obtained from racemic lactic acid only by expensive and troublesome precipitation and recrystallization of the salts of D- and L-lactic acid.

We have found that the preparation of optically pure lactic acid can be greatly simplified.

The present invention relates to a process for the preparation of optically pure D- and L-lactic acid by fermentation of an aqueous nutrient medium, which contains nitrogen, vitamins, aminoacids, sugars and trace elements, by means of a microorganism, at pH 4–6, wherein the nutrient medium contains brewers' yeast as the source of nitrogen, vitamins, aminoacids and trace elements.

Brewers' yeast contains adequate concentrations of all vitamins, proteins and trace elements required for the fermentation. Examples of suitable brewers' yeasts are *Saccharomyces cerevisiae* and *S. carlsbergensis*.

Brewers' yeast is obtained as a by-product in brewing, and its concentration in the nutrient medium is from 1 to 50, preferably from 5 to 30, g of dry substance per liter. It may be used in the form of a fresh aqueous suspension containing about 10% of dry substance, as produced by breweries, or in the form of a dry product, as supplied by companies which process brewers' yeast.

The yeast may be used directly in these forms, but it is advantageous to heat it in water for several hours at from 90° to 100° C. In another embodiment of the novel process, the brewers' yeast, in a concentration of from 1 to 10% in water, is incubated at from 30° to 60° C. for from 1 to 2 hours, in order to initiate autolysis. Proteolytic enzymes may be added, but the addition is not necessary. It is also advantageous to effect mechanical fragmentation of the cells using an apparatus such as Dynomill ®.

The nutrient medium must contain, as the carbon source, a sugar which can be degraded by the microorganisms to give lactic acid. Examples of such sugars include sucrose, lactose and glucose.

Microorganisms which are suitable for use in the novel process for the preparation of optically pure D- or L-lactic acid are those which produce only one enantiomer of lactic acid. Microorganisms of this type are mentioned in the examples, and may be obtained from depositories of microorganisms.

During fermentation of the sugar, the pH should be about 4–6, preferably 4.5–5.5, and the mixture is most readily brought to this pH by the addition of calcium carbonate in pure or industrial form, for example as whiting, ground limestone or ground marble. However, the above pH may also be obtained by adding an alkali metal hydroxide, an alkaline earth metal hydroxide or an alkali metal carbonate.

The fermentation is carried out in general in a stirred vessel which can be heated or cooled, at a temperature which is optimum for the microorganism, i.e. about 40°–60° C. In a preferred embodiment of the novel process, the above vessel is charged with water, brewers' yeast and whiting, and the mixture is boiled for about 4 hours under $N_2$. The mixture is cooled to the fermentation temperature, after which glucose is added and the mixture is inoculated with from 1 to 20% of an actively fermenting pre-culture of the microorganism employed. The fermentation is terminated when the glucose employed has been consumed. The D- or L-lactic acid can then be isolated from the fermentation mash by a conventional method, for example by acidifying the mash to pH 2 with sulfuric acid and then filtering it. The filtrate contains optically pure D- or L-lactic acid, which may be obtained in good chemical purity by concentrating the filtrate.

The novel process is very simple to carry out, and gives D- or L-lactic acid in virtually complete optical purity and in very good yields.

The Examples which follow illustrate the invention.

EXAMPLE 1

320 g of whiting, 80 g of dry brewers' yeast and 2.4 l of tap water are boiled for 4 hours in a 5 l glass fermenter, while gassing with $N_2$ and stirring. The mixture is cooled to 45° C., after which 4 g of concentrated phosphoric acid and 400 g of glucose monohydrate, which has been sterilized in 1.6 l of water at 121° C. for 15 minutes, are added, and the mixture is inoculated with 40 ml of a pre-culture, which is no more than 24 hours old, of *Lactobacillus lactis* ATCC 8000 in an MRS medium. The mixture is stirred at 45° C. under an $N_2$ atmosphere. Samples are taken at regular intervals, and their contents of Lactic acid are determined by an enzymatic method. The result is as follows:

| Fermentation time (hours) | D-lactic acid (g/l) | L-lactic acid (g/l) |
| --- | --- | --- |
| 15.5 | 11 | |
| 44 | 34 | |
| 64 | 52 | |
| 88 | 72 | |
| 96 | 78 | |
| 112 | 83 | 0.3 |

The fermentation is terminated after 112 hours, all the glucose having been consumed. The culture broth is acidified with 300 g of concentrated sulfuric acid, and filtered under suction using a filter cloth. Concentration of the filtrate gives 308 g of D-lactic acid of 99.3% optical purity.

EXAMPLE 2

4 L of a brewers' yeast medium as described in Example 1 are inoculated with 40 ml of a pre-culture, which is no more than 24 hours old, of *Lactobacillus lactis* DSM 20073 in an MRS medium at 45° C., and the mixture is stirred at 45° C. under an $N_2$ atmosphere. The formation of lactic acid takes place as follows:

| Fermentation time (hours) | D-lactic acid (g/l) | L-lactic acid (g/l) |
| --- | --- | --- |
| 15 | 37.0 | |
| 24 | 46.0 | |
| 40 | 59.0 | |
| 48 | 68.2 | |
| 64 | 81.8 | |
| 70 | 82.4 | 0 |

The fermentation is terminated after 70 hours, all the glucose having been consumed. The culture broth is acidified with 300 g of concentrated sulfuric acid, and filtered under suction using a filter cloth, and the filtrate is concentrated. The resulting D-lactic acid is 100% optically pure.

EXAMPLE 3

1 L of a brewers' yeast medium as described in Example 1, but containing only 50 g/l of glucose, is inoculated with 10 ml of an 8 hour old pre-culture of *Lactobacillus casei* IFO 3425 in an MRS medium at 40° C., and the mixture is stirred at 40° C. under an $N_2$ atmosphere. The formation of L-lactic acid is given in Table 1, the fermentation being terminated after 38 hours. The culture solution is acidified with 45 g of concentrated sulfuric acid, filtered and concentrated. The resulting L-lactic acid is more than 99% optically pure.

EXAMPLE 4

1 L of a brewers' yeast medium as described in Example 3 is inoculated with 10 ml of an 8 hour old pre-culture of *Lactobacillus casei* spp. rhamnosus DSM 20021 in an MRS medium at 40° C., and the mixture is stirred at 40° C. under an $N_2$ atmosphere. The formation of L-lactic acid is given in Table 1, the fermentation being terminated after 38 hours. The culture solution is then acidified with 45 g of concentrated sulfuric acid, filtered and concentrated. The resulting L-lactic acid is more than 99% optically pure.

TABLE 1

| Fermentations to produce lactic acid, using L. casei JFO 3425 and DSM 20021 | | | | |
| --- | --- | --- | --- | --- |
| Fermentation time (hours) | L-lactic acid (g/l) | | D-lactic acid (g/l) | |
| | JFO 3425 | DSM 20021 | JFO 3425 | DSM 20021 |
| 0 | 0 | 0 | 0 | 0 |
| 23 | 14.2 | 12.2 | 0 | 0 |
| 38 | 47.3 | 45.2 | 0.2 | 0.1 |

We claim:
1. A process for the preparation of substantially optically pure D- or L-Lactic acid comprising the steps of:
   (a) providing a sample of Lactobacilli which produces but one of the D- or L-optical isomers of Lactic acid;
   (b) providing aqueous nutrient medium for the Lactobacilli of step (a), said medium consisting of unextracted brewers' yeast in the form as obtained in conventional brewing operations which is an aqueous suspension containing about 10 percent dry solids or in the form of dry solids per se and a carbon source consisting of a sugar selected from the group consisting of sucrose, lactose and glucose;
   (c) fermenting a mixture of the Lactobacilli and the nutrient medium at a pH between about 4 and about 6 to form a substantially pure D- or L-Lactic acid product; and
   (d) isolating the substantially optically pure D- or L-Lactic acid product from said fermentation mixture.
2. A process according to claim 1, wherein the brewers' yeast is
   in the form of a fresh yeast suspension prior to preparation of the aqueous nutrient medium.
3. A process according to claim 1, wherein the brewers' yeast is in the form of a dry brewers' yeast prior to preparation of the aqueous nutrient medium.

* * * * *